United States Patent [19]

Cornsweet

[11] Patent Number: 5,114,222
[45] Date of Patent: May 19, 1992

[54] METHOD AND APPARATUS FOR PERIMETRY

[75] Inventor: Tom N. Cornsweet, Irvine, Calif.

[73] Assignee: Pulse Medical Instruments, Rockville, Md.

[21] Appl. No.: 448,550

[22] Filed: Dec. 11, 1989

[51] Int. Cl.$^5$ .............................................. A61B 3/02
[52] U.S. Cl. .................................... 351/204; 351/206; 351/211; 351/221; 351/224
[58] Field of Search ............... 351/204, 206, 211, 214, 351/221, 224

[56] References Cited

U.S. PATENT DOCUMENTS

| | | | |
|---|---|---|---|
| 4,012,128 | 3/1977 | Regan | 351/224 |
| 4,169,664 | 10/1979 | Bailey, Jr. | 351/226 |
| 4,370,033 | 1/1983 | Kani et al. | 351/214 |
| 4,822,162 | 4/1989 | Richardson et al. | 351/246 |
| 4,850,691 | 7/1989 | Gardner et al. | 351/221 |
| 5,042,937 | 8/1991 | Cornsweet | 351/204 |

Primary Examiner—Rodney B. Bovernick
Assistant Examiner—J. P. Ryan
Attorney, Agent, or Firm—Whitham & Marhoefer

[57] ABSTRACT

A perimetry system uses pupillary light response to a small bright light spot or other suitable stimulus which moves at a constant speed in generally a circular path centered on a fixation mark upon which the patient's field of view is fixed. The pattern traced by the spot may be a spiral, starting at the periphery and shrinking toward the fixation mark. A measuring system continuously monitors pupil size and if the retinal image of the moving light spot moves across a region of reduced sensitivity, this event is signaled by a change in pupil size.

10 Claims, 2 Drawing Sheets

METHOD AND APPARATUS FOR PERIMETRY

BACKGROUND OF THE INVENTION

1. Field of the Invention

This application is related in subject matter to copending application Ser. No. 07/448,718 filed Dec. 11, 1989, now U.S. Pat. No. 5,042,937, for "Pupil Function Analyzer." application Ser. No. 07/448,718 is assigned to the assignee of this application and is incorporated herein by reference.

The present invention generally relates to automated instruments for use in examination of a patient's vision, and more particularly to an improved clinical method and apparatus for identifying and measuring regions of reduced sensitivity in a patient's visual field by means of pupillary light response.

2. Description of the Prior Art

Perimetry, the identification and measurement of regions of reduced sensitivity in the visual field of an individual, is of fundamental importance in the diagnosis of a wide variety of disorders of the visual system. It is performed on a significant proportion of all patients seen by ophthalmologists. There are two types of perimetry visual field testing commonly used in the prior art; a kinetic method and a static method. Both require a judgmental response on the part of the patient.

In the kinetic method, a light spot or other suitable stimulus of a known size and brightness is moved inwardly from beyond the edge of the patient's peripheral vision until the subject signals in some manner that he or she sees the stimulus. In the static method a stationary stimulus is displayed successively at a series of points and the patient reports whether or not the stimulus is seen. If not, the brightness of the stimulus may be increased in steps with intervening pauses at each point until the patient signals that he or she sees the stimulus.

Sometimes these prior art procedures are automated and sometimes performed by hand. In either case, this procedure confronts the patient with the following task. The patient is asked to keep looking at a target straight ahead and report whether or not he or she sees other spots of light presented at different places in the visual field. Even if the task were to report whether or not a spot is visible where the patient is looking, many patients would have a difficult time making each judgment. Trying to make a judgment about seeing a spot in a location where one is careful not to look is much more difficult. The result is that for many patients their response is not reliable and the examination does not provide a good indicator of pathology.

There also have been proposals in the prior art to perform perimetry with apparatus which does not require the patient to make judgments; for example, U.S. Pat. Nos. 3,883,235 and 3,718,386. One of these proposals is to monitor pupil size as a response to the stimulus. In this procedure spots of light flash at various places in the patient's visual field while his or her pupil size is monitored electronically. A detectable change in pupil size correlated in time with a flash indicates that the visual system has detected the flash. This prior art pupillary response perimetry system is essentially the same as the widely used procedures requiring judgmental patient response except the response is pupillary rather than requiring the patient's judgment. These prior art proposals for perimetry systems using pupillary light response are not altogether practical for clinical application. The pupillary system is somewhat sluggish. After a latency of about 200 milliseconds, the response to even a brief flash of light lasts for a few seconds; the response time is a function of the intensity of the flash and the sensitivity of the device which measures pupil size. These prior art procedures can obtain measurements at the rate of only one each one or two seconds, which is comparable to the rate at which measurements can be obtained using a patient's psychophysical judgment. If pupil responses could be reliably detected, prior art pupil responsive perimetry would thus take about as long as the commonly used perimetry methods requiring patient response. However, a test spot must be fairly small if the map of the patient's field of view is to have sufficient resolution to be useful, and the pupillary response to a small spot is small. Because a pupil continuously undergoes apparently random variations in size, even in the absence of light, the small responses to flashed spots are difficult to detect reliably. To produce pupil responsive perimetry maps with prior art techniques, each location should be tested with a number of repetitions, resulting in an impractically long procedure.

SUMMARY OF THE INVENTION

It is therefore an object of this invention to provide an improved method and apparatus for performing pupillary light responsive perimetry automatically; a method and apparatus which will give results that are significantly more repeatable than with existing devices. Another object is to provide a perimetry procedure that is less anxiety engendering for the patient.

Briefly, this invention contemplates the provision of a perimetry system using pupillary light response in which the stimulus is a small bright light spot or other suitable stimulus which moves at a constant speed in generally a circular path, centered on a fixation mark upon which the patient's field of view is fixed. The pattern traced by the spot may be a spiral, starting at the periphery and shrinking toward the fixation mark. A measuring system continuously monitors pupil size and if the retinal image of the moving light spot moves across a region of reduced sensitivity, this event is signaled by a change in pupil size.

The image of the spot moves at a constant speed along a path on the retina whose distance from the fovea changes slowly so that the rate at which the spot stimulates new photoreceptors is relatively constant. It is relatively constant because the distribution of photoreceptors and associated neural circuits is circularly symmetric about the fovea. As the spot travels across healthy retina, the pupil is thusly continuously and uniformly driven to constrict. If the spot enters a region of reduced sensitivity, the pupil dilates and then constricts again as the spot exits the region. The dilation marks the point where reduced sensitivity begins and the constriction marks where it ends.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENT OF THE INVENTION

Figure 1:
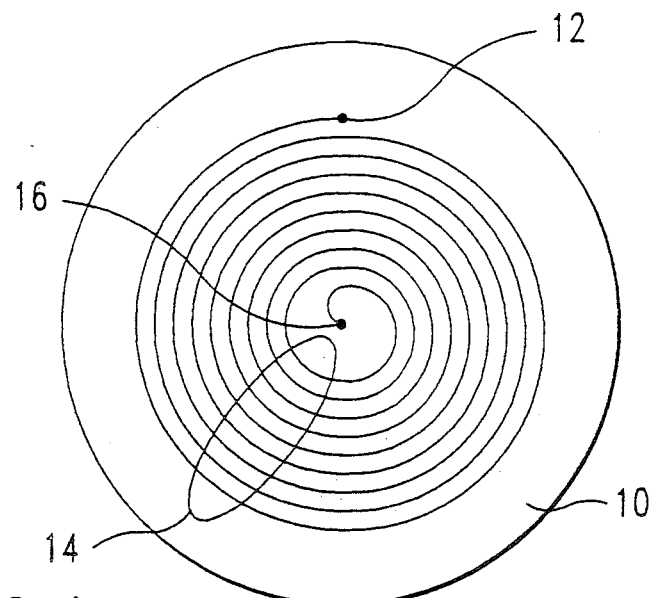
FIG. 1 is a pictorial representation of the path traced by a light spot in a perimetry system in accordance with the teachings of this invention.

Referring now to the drawings, in which the same reference numeral indicates the same element in the various figures, FIG. 1 shows the face 10 of a CRT display, for example, and a typical spiral path traced by a light spot 12 during an automated perimetry examination in accordance with this invention. The spot 12 traces a path 14 of almost concentric circles centered on a stationary light spot 16, which serves as a point upon which the patient fixes his eye. The spot 12 moves continuously and spirals inwardly toward the fixed spot during the course of an examination.

In general the spot 12 should move slowly, but at a speed at which the examination will be completed within a reasonable time. A speed to produce about 8 degrees of arc movement on the retina per second is satisfactory. A spiral in which the spot moves about 5 degrees closer to the center for each revolution is also satisfactory. It should be noted that a given area of the retina may be retraced in either direction to further examine a specific region of the retina. While a spiral path is preferred, other paths of relatively constant speed that traverse a relevant area along a path of relatively constant sensitivity can also be employed.

Figure 2:
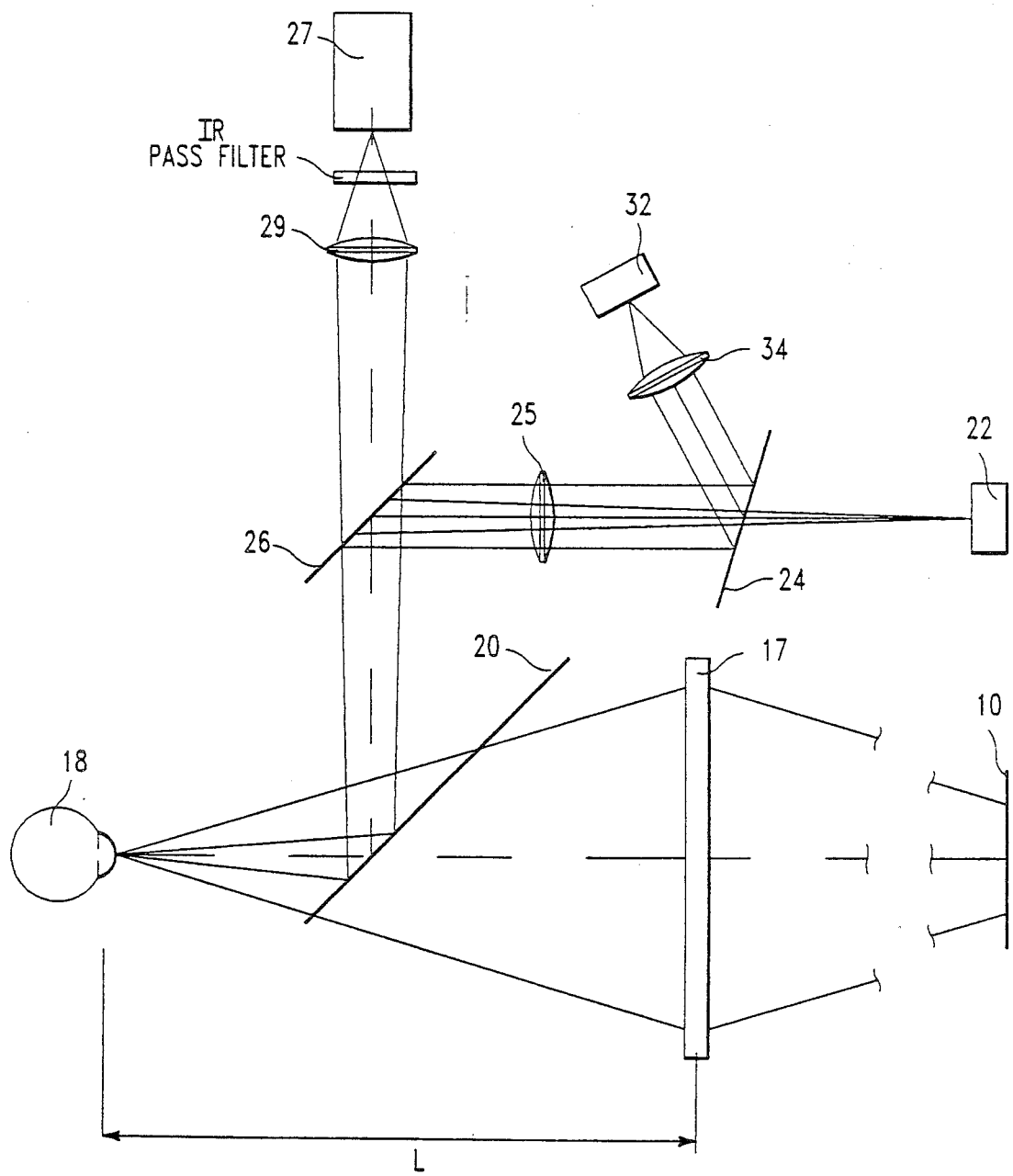
FIG. 2 is a schematic diagram of the optics for one embodiment of a perimetry system in accordance with the teachings of this invention.

Referring now to FIG. 2, the face 10 of the CRT display tube is mounted in the focal plane of lens 17 so that the spot 12 appears in focus at infinity to an eye 18 undergoing examination. For an eye with a refractive error, the face of the CRT can be moved closer to or farther from lens 17.

In the preferred embodiment of the invention, infrared light is used to detect pupillary response to the spot 12 as its image moves across the patient's retina in a path of generally concentric circles. Infrared light is also used to detect any change in the fixation of the patient's field of view, which change would invalidate a detected change in pupil size. To these ends, the patient views the screen 10 through a "hot mirror" 20. Infrared light from a pupil size measuring system and an eye position measuring system is reflected from this mirror while the stimulating visible light spot 12 and the fixation mark 16 are visible to the patient through mirror 20. While any suitable pupil size measuring systems may be used in the practice of this invention, in the preferred embodiment of the invention, the pupil size measuring system of the aforementioned Pupil Function Analyzer pending application is used. Similarly, suitable prior art eye position measuring systems may be used in the practice of this invention. The preferred embodiment of the invention uses a novel implementation of a known eye position measuring system in which reflection from the cornea of the eye under examination of an infrared source is used to detect a change in eye position.

Light from a small infrared source 22, such as an infrared LED, is used to detect changes in pupil size in the manner more fully described in the copending Pupil Function Analyzer application. Light from source 22 forms a backlighted image of the pupil whose diameter is measured by a video camera 27. To this end, light from source 22 is directed in part through a beam splitter 24 and a lens 25, is reflected in part from a second infrared beam splitter 26, and is reflected from the hot mirror 20. This optical path forms an image of the source 22 in the plane of the pupil 18. This image is smaller than the smallest pupil which would be encountered in clinical practice, (e.g., 0.25 mm). Light from source 22 goes through the pupil and illuminates a region of the retina. Light reflected from the retina that emerges from the pupil is reflected from the hot mirror 20, half then goes through the beam splitter 26 and half is reflected from the beam splitter toward lens 25 and is lost. A lens 29 forms an image of the back-lighted pupil in the plane of an infrared sensitive video camera charge coupled device (CCD) 27. The output signal of the video camera 27 may be processed in accordance with the teaching of the aforementioned Pupil Analyzer application in order to provide continuously a signal indicative of pupil size (for example diameter or area) and a signal indicative of the pupil center.

It will be appreciated that when the patient fixes his or her vision on the mark 16, the image of the mark 16 falls on the fovea of the retina. The image of the source 12 traces a path of generally concentric circles on the retina centered about the fovea. Conveniently, a map of the sensitivity of the retina can be generated by relating the position of the image of source 12 to the fovea. The location of the fovea can be determined by monitoring the direction in which the patient is looking. A convenient way to monitor where a patient is looking is to track the location of the center of the pupil in combination with the position of a corneal reflection; that is, the position of the image of a source formed by reflection from the cornea. As more fully described in the Pupil Function Analyzer application, the CRT camera 27 and the associated data processing system can determine the center of the pupil from the backlighted infrared image of the retina formed by the infrared source 22.

Cornea reflection methods for pupil position monitoring are generally known to those skilled in the art. Because the image of source 22 is very small (small enough to go through the pupil without lighting up the iris and spoiling the roundness of the image of the pupil), and because the cornea is very steeply curved, light from source 22 that is reflected from the cornea will go in a direction to pass through lens 29 only if all elements of the optical path, including the cornea, are exactly aligned. A very small decentering of the cornea will cause the reflected light to miss lens 29 altogether, thus preventing the camera 27 from seeing the corneal reflection, which in turn prevents the system from locating it.

In order to monitor corneal position, a second infrared LED source 32 is used. Preferably, source 32 is larger than source 22 and a lens 34 may be used to further magnify it so that, when focused by the optical system on the cornea, it covers a substantial portion of the area of the cornea. The optical system includes, in addition to lens 34, the beam splitter 24, lens 25, beam splitter 26 and hot mirror 20. The corneal reflection of the image of 32 is directed to the CRT camera 27 via hot mirror 20, beam splitter 26 and lens 29. As will be appreciated by those skilled in the art, the CRT camera data relating to the position of the corneal image and the position of the center of the eye can be processed using conventional data processing techniques to determine if the patient's field of vision is centered on the fixed spot 16. If it is not, information may be fed back to the patient in the form of a small arrow on the screen adjacent the spot 16 telling the patient in which direction to reorient his field of vision and the data collected while the patient's field of vision is not centered on spot 16 is discarded. It should be noted that if LED 32 were on continuously, its reflection from iris would interfere with the back-lighted image of the pupil formed by LED source 22. To avoid this problem the LEDs 32 and 22 are turned on alternately, one during one raster scan of the camera 27 and the other during the next scan of the camera. The data from the scan when LED 22 is on is used to determine pupil size and center location and the data from the alternate scan when LED 32 is on is used to determine the location of the corneal reflection.

Figure 3:
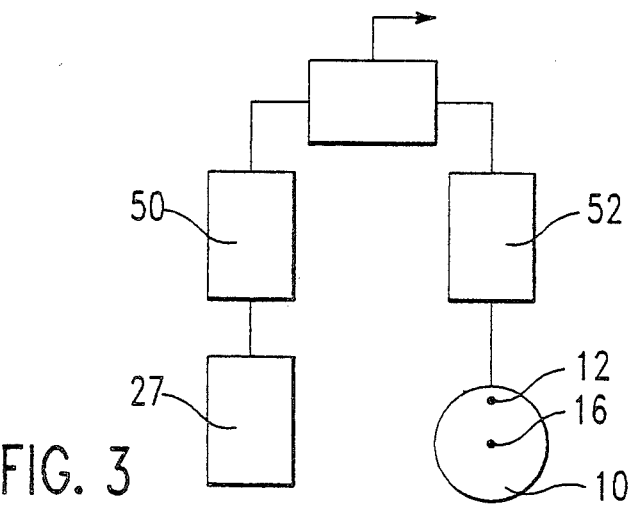
FIG. 3 is a block diagram of an embodiment of the perimetry system of this invention.
Figure 4:
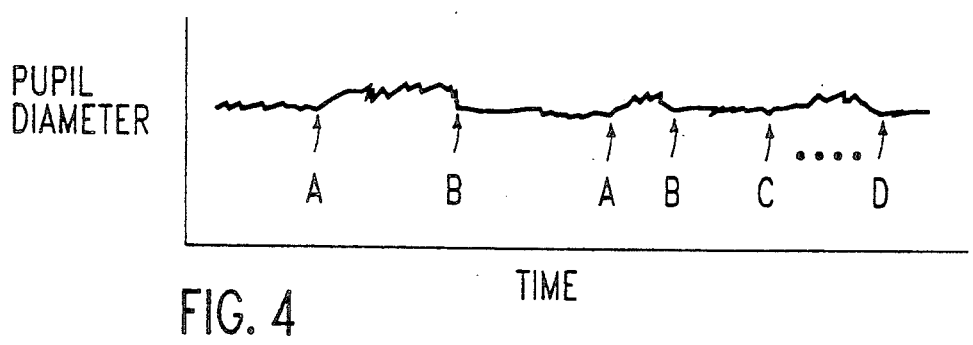
FIG. 4 is a pictorial representation of a partial output record as the result of a patient examination.

Referring now to FIGS. 3 AND 4, a suitable data processing system 50, such as disclosed in the copending Pupil Function Analyzer application, processes the output data of CCD video camera 27 in order to determine pupil size and the center of the pupil. A suitable prior art raster scan control circuit 52 controls the position of the spot 12 and the position of the spot with respect to a region of the patient's retina may be conveniently correlated on the basis of time. A suitable control and display circuit 54 may be used to generate a CRT or hard copy display of pupil size as a function of time, as shown in FIG. 4. In FIG. 4, points A and B mark respectively the beginning and end points of reduced sensitivity and resultant dilation and contraction. Points C and D illustrate a change in pupil size while the eye position is incorrect; this eye movement has been detected and denoted by marks E so that the data may be rejected and the examination in this region repeated, if desired. It will be appreciated that if desired the direction in which the patient is fixating could be determined and data as to pupil size could be thusly related to the position of the spot on the retina. However, for most applications, such a complexity is not warranted. Of course, the procedure may be completely automated and through further data processing data presented in any desired format.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A perimetry system comprising in combination;
    means for stimulating the retina of a patient's eye with a stimulating source which moves along a path of relatively constant sensitivity on the retina for a normal visual system;
    means to detect a pupillary response to said stimulating means.

2. A perimetry system as in claim 1, further including means for correlating the position of image on the retina with pupillary response.

3. A perimetry system comprising in combination;
    means for displaying a stimulating spot in the focal plane of an eye of a patient;
    means for moving said spot along a path so that the image of said spot moves along a path of relatively constant sensitivity on the retina for normal a visual system;
    means to detect a pupillary response to said stimulating means.

4. A perimetry system as in claim 3 wherein said spot moves along a spiral path of generally concentric circles.

5. A perimetry system as in claim 4 wherein said means for displaying is a cathode ray screen.

6. A perimetry system as in claim 5 further including a stimulating spot at the center of said spiral.

7. A perimetry system as in claim 6, further including means for correlating the position of image on the retina with pupillary response.

8. A perimetry system as in claim 4, further including means for correlating the position of image on the retina with pupillary response.

9. A perimetry system comprising in combination;
    means for displaying a first stimulating spot in the focal plane of the eye of a patient;
    means for moving said first spot in a spiral path of generally concentric circles centered on a second stimulating spot;
    means to detect a pupillary response to said first stimulating spot, including a first infrared source for producing a backlighted image of the pupil of the patient's eye on a scanning video detector;
    means for detecting if said eye is directed toward said fixed spot, including a second infrared source for producing a reflection from the cornea of said eye on said video detector;
    means for energizing said first and second infrared sources on alternate scans of said video detector; and
    means for correlating the position of the image of said spot on the retina with said pupillary response.

10. In a pupillary response system, the combination comprising;
    a first infrared light source for producing a backlighted image of the pupil of a patient's eye on a scanning video detector;
    a second light source for producing a reflection of the cornea of said patient's eye on said video detector; and
    means for energizing said first and second source on alternate scans of said video detector.

* * * * *